United States Patent
Eitches

(10) Patent No.: US 11,278,562 B2
(45) Date of Patent: Mar. 22, 2022

(54) HEALTH SUPPLEMENT

(71) Applicant: Dr Sari's, Inc., Los Angeles, CA (US)

(72) Inventor: Sari Eitches, Los Angeles, CA (US)

(73) Assignee: DR SARI'S, INC., Los Angeles, CA (US)

( * ) Notice: Subject to any disclaimer, the term of this patent is extended or adjusted under 35 U.S.C. 154(b) by 0 days.

(21) Appl. No.: 17/070,810

(22) Filed: Oct. 14, 2020

(65) Prior Publication Data

US 2021/0106609 A1    Apr. 15, 2021

Related U.S. Application Data

(60) Provisional application No. 62/914,845, filed on Oct. 14, 2019.

(51) Int. Cl.

| | | |
|---|---|---|
| *A61K 31/714* | (2006.01) | |
| *A61K 31/375* | (2006.01) | |
| *A61K 31/355* | (2006.01) | |
| *A61K 36/76* | (2006.01) | |
| *A61K 36/286* | (2006.01) | |
| *A61K 36/9068* | (2006.01) | |
| *A61K 36/67* | (2006.01) | |
| *A61K 36/35* | (2006.01) | |
| *A61K 36/16* | (2006.01) | |
| *A61K 36/53* | (2006.01) | |
| *A61K 45/06* | (2006.01) | |
| *A23L 33/155* | (2016.01) | |
| *A23L 33/105* | (2016.01) | |
| *A61K 47/02* | (2006.01) | |
| *A61K 47/38* | (2006.01) | |
| *A61K 31/592* | (2006.01) | |
| *A61K 31/593* | (2006.01) | |
| *A61K 33/26* | (2006.01) | |
| *A61K 33/18* | (2006.01) | |
| *A61K 31/4415* | (2006.01) | |

(52) U.S. Cl.
CPC .......... *A61K 31/714* (2013.01); *A23L 33/105* (2016.08); *A23L 33/155* (2016.08); *A61K 31/355* (2013.01); *A61K 31/375* (2013.01); *A61K 31/4415* (2013.01); *A61K 31/592* (2013.01); *A61K 31/593* (2013.01); *A61K 33/18* (2013.01); *A61K 33/26* (2013.01); *A61K 36/16* (2013.01); *A61K 36/286* (2013.01); *A61K 36/35* (2013.01); *A61K 36/53* (2013.01); *A61K 36/67* (2013.01); *A61K 36/76* (2013.01); *A61K 36/9068* (2013.01); *A61K 45/06* (2013.01); *A61K 47/02* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,586,018 B1 * | 7/2003 | Fasano | A61K 36/81 424/746 |
| 2003/0086981 A1 * | 5/2003 | Seiki | A61K 31/202 424/725 |
| 2005/0220715 A1 * | 10/2005 | Lin | A61K 45/06 424/10.1 |
| 2011/0159123 A1 * | 6/2011 | Ditchfield | A61K 31/196 424/752 |
| 2013/0202668 A1 * | 8/2013 | Prost | A61K 8/9789 424/402 |
| 2018/0193398 A1 * | 7/2018 | Johnson | A61K 36/85 |

FOREIGN PATENT DOCUMENTS

| | | | | |
|---|---|---|---|---|
| JP | 2004262922 A | * | 9/2004 | A23L 1/30 |
| WO | WO-2018065795 A1 | * | 4/2018 | A61K 31/714 |

OTHER PUBLICATIONS

Fertility Friday, Fix-Your-Period, obtained on Dec. 17, 2020 from https://fertilityfriday.com/fix-your-period/, dated Dec. 29, 2014 (Year: 2014).*

\* cited by examiner

*Primary Examiner* — Dale R Miller
(74) *Attorney, Agent, or Firm* — Cooley LLP

(57) ABSTRACT

A kit for supporting health of a user throughout the user's menstrual cycle may include at least two daily supplements of a first type, and at least two daily supplements of a second type, the second type different from the first type, wherein the daily supplements of the first type and the daily supplements of the second type are packaged in a single kit according to menstrual cycle phase. A method for supporting health of a user throughout the user's menstrual cycle may include providing at least two daily supplements of a first type, providing at least two daily supplements of a second type, and instructing the user to ingest the daily supplements of the first type during at least two days of a first time period of the menstrual cycle, and to ingest the daily supplements of the second type during at least two days of a second time period of the menstrual cycle.

20 Claims, 7 Drawing Sheets

HEALTH SUPPLEMENT

CROSS-REFERENCE TO RELATED APPLICATIONS

This application claims priority to U.S. Patent Application No. 62/914,845, filed Oct. 14, 2019, which is incorporated herein in its entirety by this reference.

TECHNICAL FIELD

This invention relates generally to the field of health supplements, such as for women's health.

BACKGROUND

Women experience fluctuating hormones, inflammatory factors, and other symptoms throughout different portions of the menstrual cycle. Many of these cyclical changes not only cause physical discomfort (e.g., cramps, bloating, inflammation, breast pain, constipation, cravings, etc.) but also emotional effects (e.g., depression, moodiness, irritability, etc.). Due to such bodily changes throughout the menstrual cycle, women have unique nutritional needs in order to support and maintain their health.

Some conventional nutritional supplements are specifically formulated for women in an attempt to address the unique nutritional needs of women. However, such nutritional supplements are typically "one size fits all" multivitamins which fail to effectively address the cyclic needs of women, which may vary from day to day. Thus there is a need for a new and improved health supplement to support women's health.

SUMMARY

A kit for supporting health of a user throughout the user's menstrual cycle may include at least two daily supplements of a first type, and at least two daily supplements of a second type, where the second type is different from the first type. The daily supplements of the first type and second type may be packaged in a single kit according to menstrual cycle phase. In some variations, the kit may further include at least two daily supplements of a third type that is different from the first and second types, and at least two daily supplements of a fourth type that is different from the first, second, and third types. In some variations, the daily supplements of the first type, second type, third type, and fourth type may be packaged in a single kit according to menstrual cycle phase.

In some variations, the daily supplements of the first type may include one or more nutrients selected from the group consisting of iron, Vitamin C, cramp bark, and ginger root. For example, the daily supplements of the first type may include a first unit dose comprising: from about 5 mg to about 15 mg chelated iron or ferrous sulfate, from about 50 to 500 mg Vitamin C, and/or from about 100 to 500 mg of cramp bark.

In some variations, the daily supplements of the second type may include one or more nutrients selected from the group consisting of Vitamin $B_{12}$, folate, iodine, Vitamin D2, Vitamin $D_3$, Vitamin $K_2$, Vitamin $K_3$, and selenium. For example, the daily supplements of the second type may include a second unit dose comprising: from about 10 mcg to about 2500 mcg of Vitamin $B_{12}$, from about 10 mcg to about 800 mcg of methyl folate or folate, from about 5 mcg to about 200 mcg of iodine, from about 100 IU to about 2500 IU of Vitamin $D_2$ or Vitamin $D_3$, and/or from about 10 mcg to about 200 mcg of Vitamin $K_2$ or $K_3$.

In some variations, the daily supplements of the third type may include one or more nutrients selected from the group consisting of chaste berry and milk thistle. For example, the daily supplements of the third type may include a third unit dose comprising: from about 40 mg to about 150 mg of chaste berry, and/or from about 50 mg to about 400 mg of milk thistle.

In some variations, the daily supplements of the fourth type may include one or more nutrients selected from the group consisting of Vitamin $B_6$, Vitamin E, *Gingko biloba*, white willow bark, an omega-3 fatty acid, ginger root, capsaicin, chamomile, valerian root, and magnesium. For example, the daily supplements of the fourth type may include a fourth unit dose comprising from about 5 mg to about 100 mg of Vitamin $B_6$, and/or from about 80 mg to about 500 mg of white willow bark. In some variations, the fourth unit dose may further include from about 100 IU to about 500 IU of Vitamin E and from about 80 mg to about 160 mg of *Gingko biloba*. Additionally or alternatively, the fourth daily supplement may include about 250 mg DHA, about 150 mg of ginger root, capsaicin, chamomile, and valerian root. Additionally or alternatively, the fourth unit dose may further include from about 50 mg to about 250 mg of magnesium citrate or magnesium glycinate.

In some variations, the daily supplements may be packaged in a single kit according to menstrual cycle phase, such as sequentially arranged in a blister pack according to menstrual cycle phase. In some variations, the blister pack may be arranged in a housing or other suitable outer packaging. For example, the housing or other outer packaging may be reclosable or resealable. Additionally or alternatively, the kit may include one or more labels identifying at least a portion of the daily supplements of the first type, the daily supplements of the second type, the daily supplements of the third type, and/or the daily supplements of the fourth type according to menstrual cycle phase. For example, the one or more labels may include a plurality of labels identifying each daily supplement of the first type and each daily supplement of the second type for ingesting on a respective assigned day of the menstrual cycle.

In some variations, the kit may include one or more labels identifying the daily supplements of the first type for ingesting during at least a portion of the time period from day 1 to day 7 of the menstrual cycle. Additionally or alternatively, in some variations the kit may include one or more labels identifying the daily supplements of the second type for ingesting during at least a portion of the time period from day 4 to day 13 of the menstrual cycle. Additionally or alternatively, in some variations the kit may include one or more labels identifying daily supplements of the third type for ingesting during at least a portion of the time period from day 11 to day 21 of the menstrual cycle. Additionally or alternatively, in some variations the kit may include one or more labels identifying daily supplements of a fourth type for ingesting during at least a portion of the time period from day 22 to day 35 of the menstrual cycle.

A method for supporting health of a user throughout the user's menstrual cycle may include providing at least two daily supplements of a first type, providing at least two daily supplements of a second type, and instructing the user to ingest the daily supplements of the first type during at least two days of a first time period of the menstrual cycle, and to ingest the daily supplements of the second type during at least two days of a second time period of the menstrual cycle. Furthermore, in some variations the method may include providing at least two daily supplements of a third type intended for ingesting during at least two days of a third time period of the menstrual cycle, providing at least two daily supplements of a fourth type intended for ingesting during at least two days of a fourth time period of the menstrual cycle, and instructing the user to ingest the daily supplements of the third type during the third time period and to ingest the daily supplements of the fourth type during the fourth time period.

In some variations, the first time period may include at least a portion of the period from day 1 to day 7 of the menstrual cycle, the second time period may include at least a portion of the period from day 4 to day 13 of the menstrual cycle, the third time period may include at least a portion of the period from day 11 to day 21 of the menstrual cycle, and the fourth time period may include at least a portion of the period from day 22 to day 35 of the menstrual cycle. However, the time periods may include any suitable portion of a menstrual cycle of any duration.

In some variations, the daily supplements of the first type comprise one or more nutrients selected from the group consisting of iron (e.g., chelated iron, ferrous sulfate), Vitamin C, cramp bark, and ginger root. In some variations, the daily supplements of the second type comprise one or more nutrients selected from the group consisting of Vitamin $B_{12}$ (e.g., methylcobalamin), folate (e.g., folate or methyl folate), iodine, Vitamin $D_2$, Vitamin $D_3$, Vitamin $K_2$, Vitamin $K_3$, and selenium. In some variations, the daily supplements of the third type comprise one or more nutrients selected from the group consisting of chaste berry and milk thistle. In some variations, the daily supplements of the fourth type comprise one or more nutrients selected from the group consisting of Vitamin $B_6$, white willow bark, Vitamin E, *Gingko biloba*, an omega-3 fatty acid, ginger root, capsaicin, chamomile, valerian root, and magnesium (e.g., magnesium citrate, magnesium glycinate).

DETAILED DESCRIPTION

Figure 1A:
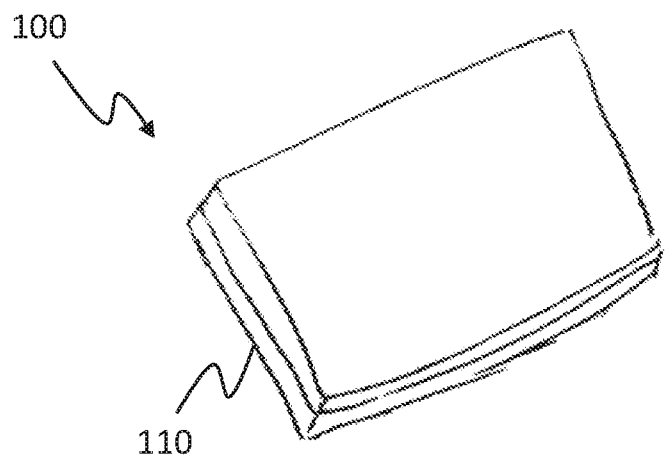
FIG. 1A depicts an exemplary variation of a kit for supporting health of a user throughout a menstrual cycle, shown in a closed state.

Non-limiting examples of various aspects and variations of the invention are described herein and illustrated in the accompanying drawings.

Provided herein are dietary supplement compositions and kits comprising one or more daily supplements of various types, where each type of daily supplement is formulated to support a user's health during a respective time period during a menstrual cycle. Methods for supporting a user's health during a menstrual cycle may include providing daily supplements of the various types throughout the menstrual cycle, and instructing the user to ingest the daily supplements during specified time periods during a menstrual cycle.

The formulations for the various types of daily supplements vary relative to the fluctuating cyclic needs, symptoms, hormones, and inflammatory factors throughout different points of time during the menstrual cycle. For example, the formulations specifically alleviate iron deficiency, hormone fluctuations, inflammation (e.g., due to prostaglandins), smooth muscle spasms, cramps, and the like. Furthermore, the formulations support ovulation and hormone metabolism.

The various types of daily supplements, when each daily supplement is ingested at an appropriate and designated time, combine to work synergistically as to reduce the total unit dose, decrease the amount excreted, and/or increase efficacy. Accordingly, the cyclic and synergistic dosing allows the user to ingest fewer supplements overall (e.g., one or two capsules daily), compared to a user who obtains separate supplements for each nutrient and must ingest a larger suite of such separate supplements each day.

Daily Supplements

In some variations, a kit for supporting health of a user throughout the user's menstrual cycle includes multiple types of daily supplements formulated to be ingested at different time periods throughout the menstrual cycle. For example, in some variations, a kit may include one or more daily supplements of a first type, supplements of a second type, supplements of a third type, and supplements of a fourth type, where each supplement type is formulated to provide certain nutritional benefits during different portions of a menstrual cycle, as further described herein.

In some variations, one or more daily supplements may be contained within a capsule shell. In some variations, the capsule shell may delay release of the supplement until the composition has passed through the stomach of a mammal (e.g., human). Some or all of the daily supplement types may be contained within capsules of similar size and/or shape, or some or all of the daily supplement types may be contained within capsules of different sizes and/or shapes.

In some variations, each type of daily supplement includes a unit dose in a single capsule. For example, all nutrients in the daily supplement may be combined to form a single nutrient composition designed to be ingested as a unit dose during a designated time period (e.g., designated day) of a menstrual cycle. This is contrast, for example, to a supplement system including each nutrient (or at least one nutrient) in a separate, respective and distinct capsule. However, it should be understood that the unit dose for a daily supplement described herein may be divided across multiple capsules; for example, two capsules (each capsule including about half of the unit dose of the nutrient composition) may be designed to be ingested on the same designated day.

Phase One

In some variations, one or more daily supplements of a first type may be designed for ingesting over a first time period of a menstrual cycle. Such a supplement may, for example, be designed for ingestion over at least part of the menstruation phase, or other first time period, of a menstrual cycle. For example, the one or more daily supplements of the first type may be designed for ingestion for a first time period beginning on day 1 (beginning of menstruation) and extending to any one of day 3, day 4, day 5, day 6, and day 7 of a menstrual cycle. The daily supplements of the first type may, for example, replete iron from blood loss and/or treat cramps.

As described above, the daily supplements of the first type include at least one nutrient. In some variations, the at least one nutrient is selected from the group consisting of iron, Vitamin C, cramp bark (vibernum *opulus*), ginger root (*Zingiber officinale*), and any combination thereof. In some variations, the daily supplement of the first type includes at least one, at least two, at least three, or at least four nutrients from the group consisting of iron, Vitamin C, cramp bark, ginger root, and any combination thereof. In some variations, the daily supplement of the first type includes iron and Vitamin C. In some variations, the daily supplement of the first type includes iron, Vitamin C, and cramp bark. In some variations, the daily supplement of the first type includes iron, Vitamin C, cramp bark, and ginger root.

In some variations, the daily supplement of the first type includes iron. The iron may be present in any suitable form, for example as an iron compound. In some variations, the iron is in the form of an iron salt. For example, the daily supplement of the first type may include chelated iron or ferrous sulfate. In some variations, the daily supplement of the first type includes between about 5 milligrams (mg) to about 15 mg, between about 5 mg to about 13.5 mg, between about 5 mg to about 11 mg, between about 7.5 mg to about 15 mg, between about 7.5 mg to about 13.5 mg, between about 7.5 mg to about 11 mg, between about 9 mg to about 15 mg, between about 9 mg to about 13.5 mg, between about 9 mg to about 11 mg, or about 10 mg of iron. It should be understood that if the composition includes, for example, 10 mg of iron, and the iron is present in the form of a chemical compound including iron, the composition may include greater than 10 mg of the chemical compound such that the total iron content of the composition is 10 mg.

In some variations, the daily supplement of the first type includes Vitamin C. Vitamin C may be present in any suitable form, such as ascorbic acid. In some variations, the daily supplement of the first type includes between about 50 mg to about 500 mg, between about 50 mg to about 400 mg, between about 50 mg to about 300 mg, between 50 mg to about 200 mg, between about 50 mg to about 150 mg, between about 50 mg to about 100 mg, between about 50 mg to about 75 mg, between about 60 mg to about 70 mg, or about 67 mg of Vitamin C. It should be understood that if the composition includes, for example, 67 mg of Vitamin C, and the Vitamin C is present in the form of a chemical compound including Vitamin C, the composition may include greater than 67 mg of the chemical compound such that the total Vitamin C content of the composition is 67 mg.

In some variations, the daily supplement of the first type includes cramp bark (vibernum *opulus*). In some variations, the daily supplement of the first type includes between about 100 mg to about 500 mg, between about 100 mg to about 400 mg, between about 100 mg to about 350 mg, between about 200 mg to about 500 mg, between about 200 mg to about 450 mg, between about 200 mg to about 400 mg, between about 200 mg to about 350 mg, between about 250 mg to about 500 mg, between about 250 mg to about 450 mg, between about 250 mg to about 400 mg, between about 250 mg to about 350 mg, between about 275 mg to about 325 mg, or about 300 mg of cramp bark.

In some variations, the daily supplement of the first type includes ginger root (*Zingiber officinale*). In some variations, the daily supplement of the first type includes between about 50 mg to about 300 mg, between about 50 mg to about 250 mg, between about 50 mg to about 200 mg, between about 75 mg to about 300 mg, between about 75 mg to about 250 mg, between about 75 mg to about 200 mg, between about 100 mg to about 200 mg, or about 150 mg of ginger root.

In some variations, the composition of daily supplement of the first type includes any suitable ratio of two or more nutrients. For example, in some variations the daily supplement of the first type may include iron and Vitamin C, and the weight ratio of iron to Vitamin C may be from about 30:180 to about 30:222. In some variations, the weight ratio of iron to Vitamin C may be from about 30:190 to about 30:210. In some variations, the weight ratio of iron to Vitamin C may be about 30:200.

Phase Two

In some variations, one or more daily supplements of a second type may be designed for ingesting during a second time period of a menstrual cycle. Such a supplement may, for example, be designed for ingestion over at least part of the proliferative phase or other second time period, of a menstrual cycle. For example, the one or more daily supplements of the second type may be designed for ingestion during a second time period beginning on any one of day 4, day 5, day 6, day 7, and day 8, and extending to any one of day 10, day 11, day 12, and day 13 of a menstrual cycle. The daily supplements of the second type may, for example, replenish vitamin stores and/or prepare for upcoming ovulation, the influx of hormones, and/or inflammation.

As described above, the daily supplements of the second type include at least one nutrient. In some variations, the at least one nutrient is selected from the group consisting of Vitamin $B_{12}$, folate, iodine, Vitamin D, Vitamin K, selenium, and any combination thereof. In some variations, the daily supplement of the second type includes at least one, at least two, at least three, at least four, at least five, or at least six nutrients from the group consisting of Vitamin $B_{12}$, folate, iodine, Vitamin D, Vitamin K, selenium, and any combination thereof. In some variations, the daily supplement of the second type includes Vitamin $B_{12}$, folate, iodine, Vitamin D, and Vitamin K. In some variations, the daily supplement of the third type includes Vitamin $B_{12}$, folate, iodine, Vitamin D, Vitamin K, and selenium. In some variations, the combination of Vitamin D and Vitamin K may synergistically support calcium utilization and/or bone strength. Additionally or alternatively, the combination of iodine and selenium may synergistically support thyroid hormone balance, such as by aiding in the conversion between thyroid hormones (e.g., triiodothyronine (T3), thyroxine (T4), etc.).

In some variations, the daily supplement of the second type includes Vitamin $B_{12}$. In some variations, the daily supplement of the second type may include Vitamin $B_{12}$ as methylcobalamin. In some variations, the daily supplement of the second type includes between about 10 micrograms (mcg) to about 2500 mcg, between about 10 mcg to about 2000 mcg, between about 10 mcg to about 1500 mcg, between about 10 mcg to about 1000 mcg, between about 500 mcg to about 2500 mcg, between about 500 mcg to about 2000 mcg, between about 500 mcg to about 1500 mcg, or about 1000 mcg of Vitamin $B_{12}$. It should be understood that if the composition includes, for example, 1000 mcg of Vitamin $B_{12}$, and the Vitamin $B_{12}$ is present in the form of a chemical compound including Vitamin $B_{12}$, the composition may include greater than 1000 mcg of the Vitamin $B_{12}$ compound such that the total Vitamin $B_{12}$ content is 1000 mcg.

In some variations, the daily supplement of the second type includes folate. In some variations, the daily supplement of the second type may include folate as methyl folate. In some variations, the daily supplement of the second type includes between about 10 mcg to about 800 mcg, between about 10 mcg to about 700 mcg, between about 10 mcg to about 600 mcg, between about 10 mcg to about 500 mcg, between about 100 mcg to about 800 mcg, between about 100 mcg to about 700 mcg, between about 100 mcg to about 600 mcg, between about 100 mcg to about 500 mcg, between about 200 mcg to about 800 mcg, between about 200 mcg to about 700 mcg, between about 200 mcg to about 600 mcg, between about 200 mcg to about 600 mcg, between about 200 mcg to about 500 mcg, between about 300 mcg to about 800 mcg, between about 300 mcg to about 700 mcg, between about 300 mcg to about 600 mcg, between about 300 mcg to about 500 mcg, or about 400 mcg of folate. It should be understood that if the composition includes, for example, 400 mcg of folate, and the folate is present in the form of a chemical compound including folate, the composition may include greater than 400 mcg of folate such that the total folate content is 400 mcg.

In some variations, the daily supplement of the second type includes iodine. The iodine may be present in any suitable form, for example as an iodine compound. In some variations, the iodine is an iodine salt, for example, sodium iodide or potassium iodide. In some variations, the iodine comprises molecular iodine from one or more plant-based sources such as kelp (e.g., kelp powder). In some variations, the daily supplement of the second type includes between about 5 mcg to about 200 mcg, between about 50 mcg to about 200 mcg, between about 100 mcg to about 200 mcg, or about 150 mcg of iodine. For example, the daily supplement of the second type may include between about 0.1 mg and about 0.2 mg of kelp powder (with 0.3% iodine). It should be understood that if the composition includes, for example, 150 mcg of iodine, and the iodine is present in the form of a chemical compound including iodine, the composition may include greater than 150 mcg of the iodine compound such that the total iodine content is 150 mcg.

In some variations, the daily supplement of the second type includes Vitamin D. The daily supplement of the second type may include Vitamin $D_3$ and/or Vitamin $D_2$. The Vitamin D may be present in any suitable form, for example as cholecalciferol or ergocalciferol. In some variations, the daily supplement of the second type includes between about 100 IU to about 2500 IU, between about 100 IU to about 2000 IU, between about 100 IU to about 1500 IU, between about 500 IU to about 2500 IU, between about 500 IU to about 2000 IU, between about 500 IU to about 1500 IU, or about 1000 IU of Vitamin D. It should be understood that if the composition includes, for example, 1000 IU of Vitamin D, and the Vitamin D is present in the form of a chemical compound including Vitamin D, the composition may include greater than 1000 IU of the Vitamin D compound such that the total Vitamin D content is 1000 IU.

In some variations, the daily supplement of the second type includes Vitamin K. The daily supplement of the second type may include Vitamin $K_2$ and/or Vitamin $K_3$. The Vitamin K may be in any suitable form, for example as menaquinone-4 or menaquinone-7. In some variations, the daily supplement includes between about 10 IU to about 200 IU, between about 10 IU to about 175 IU, between about 10 IU to about 150 IU, between about 10 IU to about 125 IU, between about between about 50 IU to about 200 IU, between about 50 IU to about 175 IU, between about 50 IU to about 150 IU, between about 50 IU to about 125 IU, between about 75 IU to about 200 IU, between about 75 IU to about 175 IU, between about 75 IU to about 150 IU, between about 75 IU to about 125 IU, or about 100 IU of Vitamin K. In some variations, the daily supplement includes 10 mg to about 200 mg, between about 10 mg to about 175 mg, between about 10 mg to about 150 mg, between about 10 mg to about 125 mg, between about between about 50 mg to about 200 mg, between about 50 mg to about 175 mg, between about 50 mg to about 150 mg, between about 50 mg to about 125 mg, between about 75 mg to about 200 mg, between about 75 mg to about 175 mg, between about 75 mg to about 150 mg, between about 75 mg to about 125 mg, or about 100 mg of Vitamin K. It should be understood that if the composition includes, for example, 100 mg of Vitamin K, and the Vitamin K is present in the form of a chemical compound including Vitamin K, the composition may include greater than 100 mg of the Vitamin K compound such that the total Vitamin K content of the composition is 100 mg.

In some variations, the daily supplement of the second type includes selenium. The selenium may be in any suitable form, such as an organic selenium compound. In some variations, the daily supplement of the second type includes between about 50 mcg to about 200 mcg, between about 50 mcg to about 175 mcg, between about 50 mcg to about 150 mcg, between about 50 mcg to about 125 mcg, between about 75 mcg to about 200 mcg, between about 75 mcg to about 175 mcg, between about 75 mcg to about 150 mcg, between about 75 mcg to about 125 mcg, or about 100 mcg of selenium. It should be understood that if the composition includes, for example, 100 mcg of selenium, and the selenium is present in the form of a chemical compound including selenium, the composition may include greater than 100 mcg of the selenium compound such that the total selenium content of the composition is 100 mcg.

In some variations, the composition of daily supplement of the second type includes any suitable ratio of two or more nutrients. For example, in some variations, the daily supplement of the second type may include Vitamin $D_3$ and Vitamin $K_2$, and the IU ratio of Vitamin $D_3$ to Vitamin $K_2$ may be from about 250:1 to about 1:2. In some variations, the IU ratio of Vitamin $D_3$ to Vitamin $K_2$ may be from about 100:1 to about 1:1. In some variations, the IU ratio of Vitamin $D_3$ to Vitamin $K_2$ may be from about 50:1 to about 1:1. In some variations, the IU ratio of Vitamin $D_3$ to Vitamin $K_2$ may be about 10:1. As another example, in some variations, the daily supplement of the second type may include iodine and selenium, and the weight ratio of iodine to selenium may be from about 4:1 to about 1:2. In some variations, the weight ratio of iodine to selenium may be from about 3:1 to about 1:1. In some variations, the weight ratio of iodine to selenium may be about 3:2.

Phase Three

In some variations, one or more daily supplements of a third type may be designed for ingesting during a third time period of a menstrual cycle. Such a supplement may, for example, be designed for ingestion over at least part of the ovulation phase and/or luteal phase, or other third time period, of a menstrual cycle. For example, the one or more daily supplements of the third type may be designed for ingestion during a third time period beginning on any one of day 11, day 12, day 13, and day 14 and extending to day 21 of a menstrual cycle. For example, the daily supplements of the third type may, for example, support the liver in metabolizing influx of hormones and to mitigate the effect of such hormones.

As described above, the daily supplements of the third type include at least one nutrient. In some variations, the at least one nutrient is selected from the group consisting of chaste berry (*Vitex agnus*), milk thistle (silymarin), and any combination thereof. In some variations, the daily supplement of the third type includes at least one or at least two nutrients selected from the group consisting of chaste berry and milk thistle. In some variations, the daily supplement of the third type includes both chaste berry and milk thistle. In some variations, the combination of chaste berry and milk thistle may work together to decrease estrogen levels. For example, chaste berry may decrease pituitary stimulation of the ovaries, and/or milk thistle may support liver metabolism.

In some variations, the daily supplement of the third type includes chaste berry (*Vitex agnus*). In some variations, the daily supplement of the third type includes between about 40 mg to about 150 mg, between about 40 mg to about 140 mg, between about 40 mg to about 130 mg, between about 40 mg to about 125 mg, between about 40 mg to about 120 mg, between about 40 mg to about 115 mg, between about 40 mg to about 110 mg, between about 50 mg to about 150 mg, between about 60 mg to about 130 mg, between 70 mg to about 120 mg, between about 80 mg to about 110 mg, or about 100 mg, between about 40 mg to about 75 mg, between about 40 mg to about 70 mg, between about 40 mg to about 65 mg, between about 45 mg to about 80 mg, between about 45 mg to about 75 mg, between about 45 mg to about 70 mg, between about 45 mg to about 65 mg, between about 50 mg to about 80 mg, between about 50 mg to about 75 mg, between about 50 mg to about 70 mg, between about 50 mg to about 65 mg, between about 55 mg to about 80 mg, between about 55 mg to about 75 mg, between about 55 mg to about 70 mg, between about 55 mg to about 80 mg, between about 55 mg to about 75 mg, between about 55 mg to about 70 mg, between about 55 mg to about 65 mg, or about 60 mg of chaste berry.

In some variations, the daily supplement of the third type includes milk thistle (silymarin). In some variations, the daily supplement of the third type includes between about 50 mg to about 400 mg, between about 50 mg to about 350 mg, between about 50 mg to about 300 mg, between about 50 mg to about 250 mg, between about 50 mg to about 200 mg, between about 50 mg to about 150 mg, or about 100 mg, between about 100 mg to about 350 mg, between about 100 mg to about 300 mg, between about 100 mg to about 250 mg, between about 100 mg to about 200 mg, between about 100 mg to about 180 mg, between about 100 mg to about 160 mg, between about 120 mg to about 400 mg, between about 120 mg to about 350 mg, between about 120 mg to about 300 mg, between about 120 mg to about 250 mg, between about 120 mg to about 200 mg, between about 120 mg to about 180 mg, between about 120 mg to about 160 mg, or about 140 mg of milk thistle.

In some variations, the composition of daily supplement of the third type includes any suitable ratio of two or more nutrients. For example, in some variations the daily supplement of the third type may include chaste berry and milk thistle, and the weight ratio of chaste berry to milk thistle may be from about 1:2 to about 2:1. In some variations, the weight ration of chaste berry to milk thistle may be about 1:10. In some variations, the weight ratio of chaste berry to milk thistle may be from 1:4 to about 3:4. In some variations, the weight ratio of chaste berry to milk thistle may be from about 1:3 to about 1:2. In some variations, the weight ratio of chaste berry to milk thistle may be about 30:70.

Phase Four

In some variations, one or more daily supplements of a fourth type may be designed for ingesting during a third time period of a menstrual cycle. Such a supplement may, for example, be designed for ingestion over at least part of the luteal phase and/or premenstrual phase, or other fourth time period, of a menstrual cycle. For example, the one or more daily supplements of the fourth type may be designed for ingestion during a fourth time period beginning on day 22 and extending to any one of day 28, day, 29, day 30, day 31, day 32, day 33, day 34, day 35, and subsequent days of a menstrual cycle. The daily supplements of the fourth type may, for example, promote muscle relaxation and decrease inflammation, decreasing fluid retention, decreasing breast tenderness, decreasing weight gain, targeting prostaglandins and/or alleviating premenstrual syndrome (PMS), constipation, and/or hormonal symptoms.

As described above, the daily supplements of the fourth type include at least one nutrient. In some variations, the at least one nutrient is selected from the group consisting of Vitamin $B_6$, Vitamin E, *Gingko biloba*, salicylic acid, an omega-3 fatty acid, ginger root, capsaicin, chamomile, valerian root, magnesium, and any combination thereof. In some variations, the daily supplement of the fourth type includes at least one, at least two, at least three, at least four, at least five, at least six, at least seven, at least eight, at least nine, or at least ten nutrients selected from the group consisting of Vitamin $B_6$, Vitamin E, *Gingko biloba*, salicylic acid, an omega-3 fatty acid, ginger root, capsaicin, chamomile, valerian root, magnesium, and any combination thereof. In some variations, the daily supplement of the fourth type includes Vitamin $B_6$, Vitamin E, *Gingko biloba*, and salicylic acid. In some variations, the daily supplement of the fourth type includes Vitamin $B_6$, salicylic acid, an omega-3 fatty acid, ginger root, capsaicin, chamomile, and valerian root. In some variations, the daily supplement of the fourth type includes Vitamin $B_6$, salicylic acid, and magnesium.

In some variations, the daily supplement of the fourth type includes Vitamin $B_6$. The Vitamin $B_6$ may be in any suitable form, for example as pyridoxal-5-phosphate. Vitamin $B_6$ may help support mood. In some variations, the daily supplement of the fourth type includes between about 5 mg to about 100 mg, between about 5 mg to about 80 mg, between about 5 mg to about 60 mg, between about 20 mg to about 100 mg, between about 20 mg to about 80 mg, between about 20 mg to about 60 mg, between about 40 mg to about 100 mg, between about 40 mg to about 80 mg, between about 40 mg to about 60 mg, or about 50 mg of Vitamin $B_6$. It should be understood that if the composition includes, for example, 50 mg of Vitamin $B_6$, and the Vitamin $B_6$ is present in the form of a chemical compound including Vitamin $B_6$, the composition may include greater than 50 mg of the Vitamin $B_6$ compound such that the total Vitamin $B_6$ content of the composition is 50 mg.

In some variations, the daily supplement of the fourth type includes salicylic acid. The salicylic acid may be in any suitable form, for example as white willow bark. In some variations, the daily supplement of the fourth type includes between about 80 mg to about 500 mg, between about 80 mg to about 450 mg, between about 80 mg to about 400 mg, between about 80 mg to about 350 mg, between about 80 mg to about 300 mg, between about 80 mg to about 250 mg, between about 100 mg to about 500 mg, between about 100 mg to about 450 mg, between about 100 mg to about 400 mg, between about 100 mg to about 350 mg, between about 100 mg to about 300 mg, between about 100 mg to about 250 mg, 150 mg to about 500 mg, between about 150 mg to about 450 mg, between about 150 mg to about 400 mg, between about 150 mg to about 350 mg, between about 150 mg to about 300 mg, between about 150 mg to about 250 mg, between about 200 mg to about 500 mg, between about 200 mg to about 450 mg, between about 200 mg to about 400 mg, between about 200 mg to about 350 mg, between about 200 mg to about 300 mg, or about 240 mg of salicylic acid. It should be understood that if the composition includes, for example, 240 mg of salicylic acid, and the salicylic acid is present in the form of a chemical compound including salicylic acid, the composition may include greater than 240 mg of the salicylic acid compound such that the total salicylic acid content of the composition is 240 mg.

In some variations, the daily supplement of the fourth type may include one or more of Vitamin E and *Gingko biloba*. The synergy of Vitamin E, salicylic acid, and *Ginkgo biloba* may help prevent and treat PMS symptoms. Vitamin E may, for example, help reduce inflammation. The Vitamin E may be in any suitable form, for example, as d-alpha tocopherol or mixed tocopherols. In some variations, the daily supplement of the fourth type includes between about 100 IU to about 500 IU, between about 100 IU to about 400 IU, between about 100 IU to about 300 IU, between about 100 IU to about 200 IU, or about 150 IU, or between about 400 IU to about 475 IU, between about 400 IU to about 450 IU, between about 400 IU to about 425 IU, or about 400 IU of Vitamin E. It should be understood that if the composition includes, for example, 150 IU of Vitamin E, and the Vitamin E is present in the form of a chemical compound including Vitamin E, the composition may include greater than 150 IU of the Vitamin E compound such that the total Vitamin E content of the composition is 150 IU.

In some variations, the daily supplement of the fourth type includes *Gingko biloba*. *Gingko biloba* may, for example, help decrease fluid retention, breast tenderness, and/or weight gain. The *Gingko biloba* may be in any suitable form, for example as *Gingko biloba* extract. In some variations, the daily supplement of the fourth type include between about 80 mg to about 160 mg, between about 100 mg to about 160 mg, between about 90 mg to about 150 mg, between about 100 mg to about 140 mg, or about 120 mg of *Gingko biloba*.

In some variations, the daily supplement of the fourth type may include one or more of an omega-3 fatty acid, ginger root, capsaicin, chamomile, and valerian root instead of Vitamin E and *Gingko biloba*. For example, in some variations the daily supplement of the fourth type may include at least one omega-3 fatty acid, ginger root, capsaicin, chamomile, and valerian root. For example, in some variations, the daily supplement of the fourth type includes an omega-3 fatty acid such as DHA or EPA. In some variations, the daily supplement of the fourth type includes between about 200 mg to about 300 mg, between about 200 mg to about 275 mg, between about 225 mg to about 300 mg, between about 225 mg to about 275 mg, or about 250 mg of DHA. In some variations, the daily supplement of the fourth type includes between about 200 mg and about 500 mg of EPA. It should be understood that one or more omega-3 fatty acids (e.g., both DHA and EPA) may be combined for a similar nutritional effect.

In some variations, the daily supplement of the fourth type includes ginger root. In some variations, the daily supplement of the fourth type includes between about 50 mg to about 250 mg, between about 75 mg to about 225 mg, between about 100 mg to about 200 mg, between about 125 mg to about 175 mg, or about 150 mg of ginger root.

In some variations, the daily supplement of the fourth type includes capsaicin. In some variations, the daily supplement of the fourth type includes between about 50 mg to about 200 mg, between about 75 mg to about 175 mg, between about 100 mg to about 200 mg, between about 125 mg to about 175 mg, or about 150 mg of capsaicin.

In some variations, the daily supplement of the fourth type includes chamomile. In some variations, the daily supplement of the fourth type includes between about 100 mg to about 300 mg, between about 150 mg to about 250 mg, between about 200 mg to about 300 mg, between about 200 mg to about 275 mg, between about 175 mg to about 275 mg, between about 210 mg to about 230 mg, or about 220 mg of chamomile.

In some variations, the daily supplement of the fourth type includes valerian root. In some variations, the daily supplement of the fourth type includes between about 100 mg and about 500 mg of valerian root, between about 150 mg and about 450 mg, between about 200 mg and about 400 mg, between about 250 mg and about 350 mg, or about 300 mg of valerian root.

In some variations, the daily supplement of the fourth type includes magnesium, instead of Vitamin E and/or *Gingko biloba*, or instead of an omega fatty-3 acid, ginger root, capsaicin, chamomile, and/or valerian root. The magnesium may be in any suitable form, for example as magnesium citrate or magnesium glycinate. In some variations, the daily supplement of the fourth type includes between about 50 mg to about 250 mg, between about 50 mg to 225 mg, between about 75 mg to about 250 mg, between about 75 mg to about 225 mg, between about 100 mg to about 250 mg, between about 100 mg to about 225 mg, between about 125 mg to about 250 mg, between about 125 mg to about 225 mg, between about 150 mg to about 250 mg, between about 150 mg to about 225 mg, between about 175 mg to about 250 mg, between about 175 mg to about 225 mg, or about 200 mg of magnesium. It should be understood that if the composition includes, for example, 200 mg of magnesium, and the magnesium is present in the form of a chemical compound including magnesium, the composition may include greater than 200 mg of the magnesium compound such that the total magnesium content of the composition is 200 mg.

In some variations, the composition of daily supplement of the fourth type includes any suitable ratio of two or more nutrients. For example, in some variations the daily supplement of the fourth type may include Vitamin $B_6$ and magnesium, and the weight ratio of Vitamin $B_6$ to magnesium may be from about 1:3.8 to about 1:4.2. In some variations, the weight ratio of Vitamin $B_6$ to magnesium may be from about 1:3.9 to about 1:4.1. In some variations, the weight ratio of Vitamin $B_6$ to magnesium may be about 1:4.

Additives

In addition to various nutrients as described above, daily supplements may include one or more additives. For example, a daily supplement of the first type, second type, third type, and/or fourth type may include magnesium stearate, which may function, for example, as a lubricant that helps improve consistency and quality control of the daily supplement. A daily supplement may include any suitable amount of magnesium stearate, such as between about 5 mg and about 25 mg. Furthermore, daily supplements of different types may include different amounts of magnesium stearate. For example, a daily supplement of the first type as described above may include about 12 mg of magnesium stearate, a daily supplement of the third type as described above may include about 5 mg of magnesium stearate, and/or a daily supplement of the fourth type as described above may include about 20 mg of magnesium stearate.

As another example, a daily supplement of the first type, second type, third type, and/or fourth type may additionally or alternatively include microcrystalline cellulose (MCC), which may function, for example, as an anti-caking agent, stabilizer, texture modifier, and/or suspending agent in the daily supplement. Suitable forms of MCC may include, for example, Endurance® MCC available from FMC Corporation, Philadelphia, Pa. A daily supplement may include any suitable amount of MCC, such as between about 25 mg to about 250 mg. Furthermore, daily supplements of different types may include different amounts of MCC. For example, a daily supplement of the first type and/or fourth type as described above may include about 50 mg of MCC, and/or a daily supplement of the third type as described above may include about 210 mg of MCC.

As another example, a daily supplement of the first type, second type, third type, and/or fourth type may additionally or alternatively include silicon dioxide ($SiO_2$, also known as silica). Silica may function, for example, as a conditioning agent, a flow agent or carrier, and/or anti-caking agent in the daily supplement. Example forms of silica include hydrophilic fumed silica (e.g., Cabosil® M5, available from Cabot Corporation, Boston, Mass.), hydrated silica (e.g., Zeofree® available from Glenn Corporation, Warwick, R.I., or Sipernat® 22 S available from Evonik Corporation, Parippany, N.J.), etc. A daily supplement may include any suitable amount of silica, such as between about 1 mg and about 15 mg. Furthermore, daily supplements of different types may include different amounts of silica. For example, a daily supplement of the first type as described above may include about 14 mg of hydrophilic fumed silica and about 10 mg of hydrated silica, a daily supplement of the third type as described above may include about 5 mg of hydrated silica, and/or a daily supplement of the fourth type as described above may include about 3 mg of hydrated silica.

Kit

One or more of the daily supplements of different types described herein may be included as part of a kit. For example, a kit may include one or more daily supplements of a first type, and one or more daily supplements of a second type different from the first type, where the daily supplements of the first type and the daily supplements of the second type are packaged in a single kit according to menstrual cycle phase (e.g., respective time periods or portions of a menstrual cycle). In some variations, the kit may further include one or more daily supplements of a third type (different from the first and second types) and/or one or more daily supplements of a fourth type (different from the first, second, and third types), where the daily supplements of the first, second, third, and/or fourth types are packaged in a single kit according to menstrual cycle phase. Furthermore, in some variations, the kit may include one or more labels identifying at least a portion of the daily supplements of the first type, second type, third type, and/or fourth type according to menstrual cycle phase. The single kit may contain a supply of daily supplements of different types for use during an entire menstrual cycle, or portions thereof (e.g., a week, two weeks, three weeks, etc.). In some variations, a single daily supplement (e.g., one capsule per day) is labeled for ingestion for a particular day (or phase or time period) in the menstrual cycle. Alternatively, a unit dose may be divided into multiple daily supplements (e.g., two capsules per day, three capsules per day, four capsules per day, etc.) and labeled for ingestion for a particular day (or phase or time period) in the menstrual cycle.

In some variations, the first type, second type, third type, and fourth type of daily supplements are similar to those described herein. For example, each daily supplement type may integrate multiple nutrients into a single composition, which reduces the need for a user to separately ingest multiple capsules each day to intake the equivalent combination and amount of nutrients.

Housing

As described above, in some variations, the kit may include a housing configured to house daily supplements. The housing may be reclosable and operable between a closed state and an open state. In the closed state, the housing may be configured to protect the contents therein, and facilitate transport of the kit. For example, it may be convenient to transport or store the kit when the housing is in the closed state, such as in a handbag, purse, luggage, in a drawer, on a shelf, etc. while protecting the daily supplements housed within the housing. The housing may include a locking mechanism to secure the housing in the closed state (e.g., latch, fastener). In the open state, the housing may be configured to enable access to the contents such as the daily supplements.

In some variations, the housing may be configured to be disposable. In other variations, the housing may be configured to be reusable. For example, although the housing becomes depleted of daily supplements as the daily supplements contained therein are consumed, the housing may be refillable with new sets of daily supplements. For example, a user may receive a menstrual cycle's worth of new daily supplements, which may replace the prior month's set of daily supplements that have been consumed. In some variations, a user may receive regular shipments of daily supplements (e.g., monthly) to replace consumed daily supplements within a reusable housing.

Figure 1B:
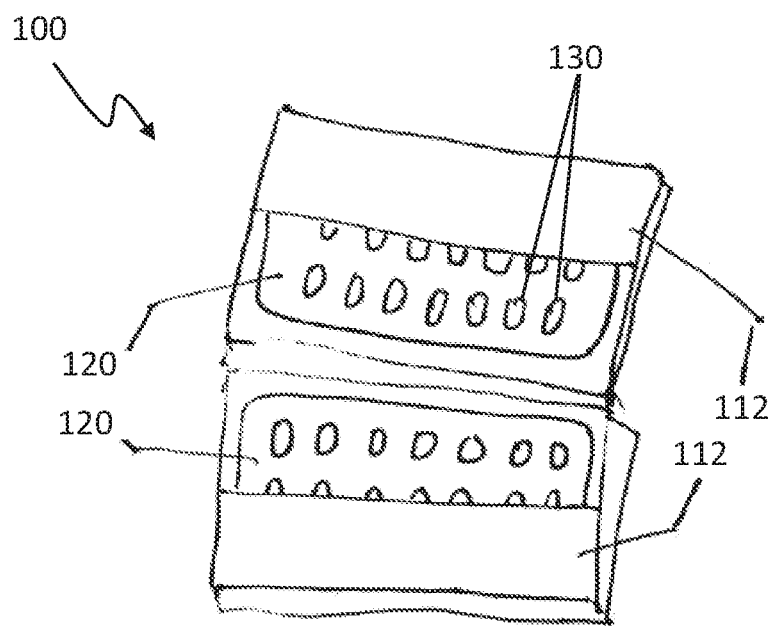
FIG. 1B depicts the kit of FIG. 1A, shown in an open state.

In some variations, as shown in FIGS. 1A and 1B, a kit 100 may include a housing 110 with one or more pockets 112. In the example shown in FIGS. 1A and 1B, the housing 110 includes a folder structure with multiple pockets 112 that receive daily supplements 130. When closed (FIG. 1A), the folder structure arranges the pockets 112 against each other to help contain daily supplements 130 within the housing. When open (FIG. 1B), the folder structure displays the daily supplements 130 for selection. In some variations, as shown in FIG. 1B, the housing 110 may include two pockets 112, each pocket including a portion of the daily supplements 130 in the kit. The two pockets 112 may be connected by a hinge, flap, or other suitable joint. In some variations, the joint may be reinforced against bending fatigue, such as by having an increased thickness, being made from a more fatigue-resistant material, and/or being reinforced with one or more ribs or backing members. At least one arrangement of daily supplements 120 (e.g., a packet such as a blister pack, as described below) may be stored in a pocket. Multiple arrangements of daily supplements (e.g., multiple packets) may be stored in a single pocket, or each arrangement of daily supplements may be stored in a different, respective pocket.

Figure 1C:
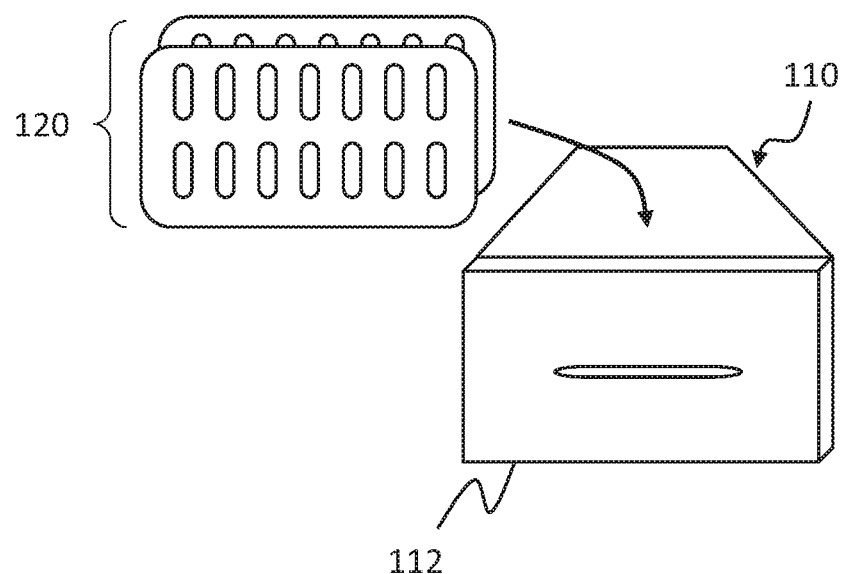
FIG. 1C depicts another exemplary variation of a kit for supporting health of a user throughout a menstrual cycle.
Figure 1D:
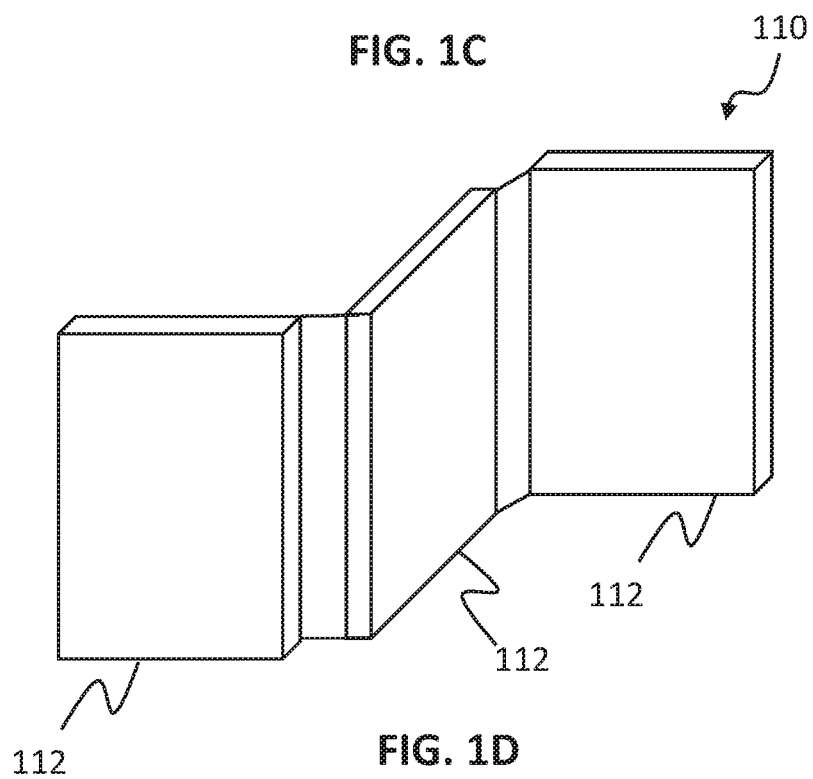
FIG. 1D depicts another exemplary variation of a housing in a kit for supporting health of a user throughout a menstrual cycle.

Although two pockets 112 are illustrated in a bifold housing configuration FIG. 1B, it should be understood that the housing 110 may include any suitable number of pockets (e.g., one, three, four, or more). For example, as shown in FIG. 1C, the housing 110 may include a single pocket 112 that may be enclosed with a flap. The flap may also include a locking mechanism for securing the housing 110 in a closed state. For example, at least a portion of the flap may be inserted into a slot or other opening on the opposite side of the pocket 112. As another example, as shown in FIG. 1C, the housing 110 may include three pockets 112 arranged in a trifold configuration. The trifold configuration may fold or otherwise collapse into a closed state in an alternating or accordion manner, for example. In another example, the housing may include three or more (four, five, or more, etc.) pockets arranged in a book configuration, where the three or more pockets are joined along a common spine joint. For example, the housing 110 may include four pockets, where each pocket may receive an arrangement of daily supplements of a respective type (e.g., a first pocket receives daily supplements of a first type, a second pocket receives daily supplements of a second type, etc.).

In some variations, individual pockets 112 may be joined to other pockets or other portions of the housing 110 with one or more perforations such that once the daily supplements 130 in a particular pocket 112 are consumed, thereby emptying the pocket 112 of daily supplements, the emptied pocket 112 may be torn off and discarded. The removal of emptied pockets 112 may, for example, make the remaining portion of the housing more compact and convenient for transport or storage, etc.

Figure 3A:
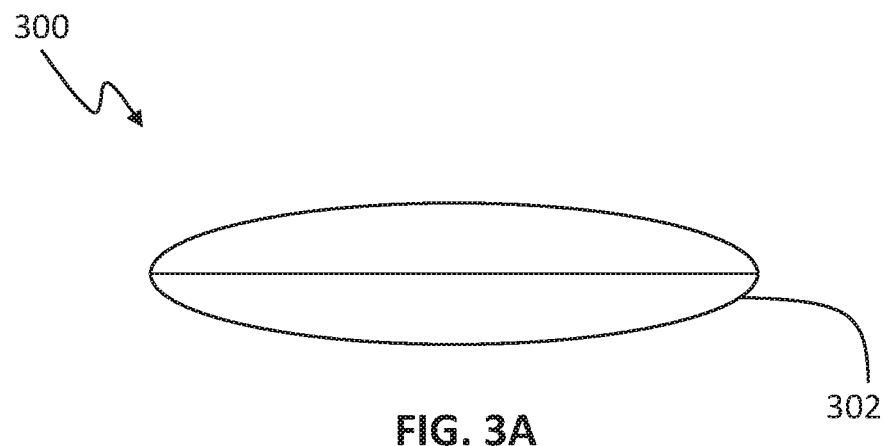
FIG. 3A depicts another exemplary variation of a kit for supporting health of a user throughout a menstrual cycle, shown in a closed state.
Figure 3B:
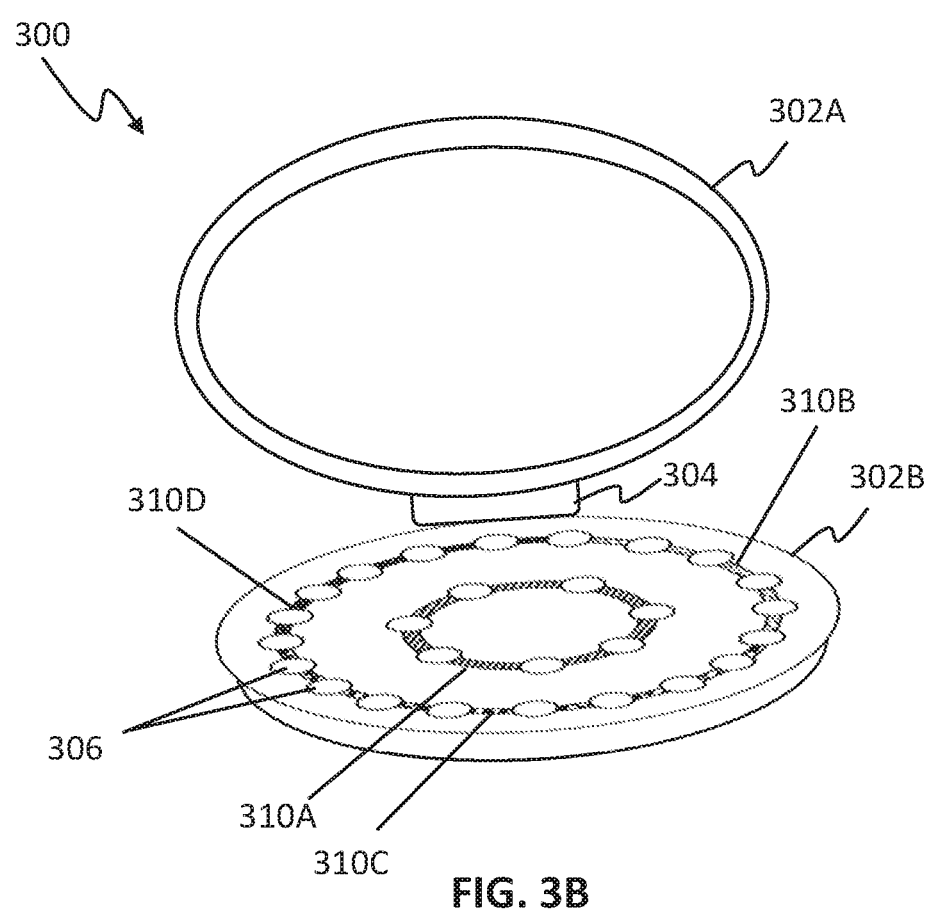
FIG. 3B depicts the kit of FIG. 3A, shown in an open state.

FIGS. 3A and 3B illustrate another exemplary variation of a kit 300 including a housing 302 comprising one or more wells 306 for storing daily supplements. Kit 300 includes a housing 302 including a first housing portion 310A and a second housing portion 310B connected at a joint 304 such as a hinge. Instead of having pockets as shown and described above with respect to FIGS. 1A-1D, one or both of the housing portions 310A and 310B may include one or more wells 306 that each directly receives a unit dose of daily supplements. For example, a well may be sized and shaped to secure an individual daily supplement with an interference fit that is tight enough to retain the daily supplement, but loose enough to enable a user to grasp the daily supplement and remove it from its well (e.g., for ingesting). Alternatively, a well may be sized and shaped to hold any suitable daily dose (e.g., two supplements). In some variations, the one or more wells may be covered with a seal (e.g., plastic film, foil, etc.) that may be peeled off or punctured to enable removal of the daily supplements (e.g., just prior to ingestion). Such a seal may help maintain sterility and/or efficacy of the daily supplement(s) and/or help retain the daily supplement(s) contained within the well, for example. Each well may have a respective seal, or one or more groups of multiple wells may have a respective seal.

Figure 4:
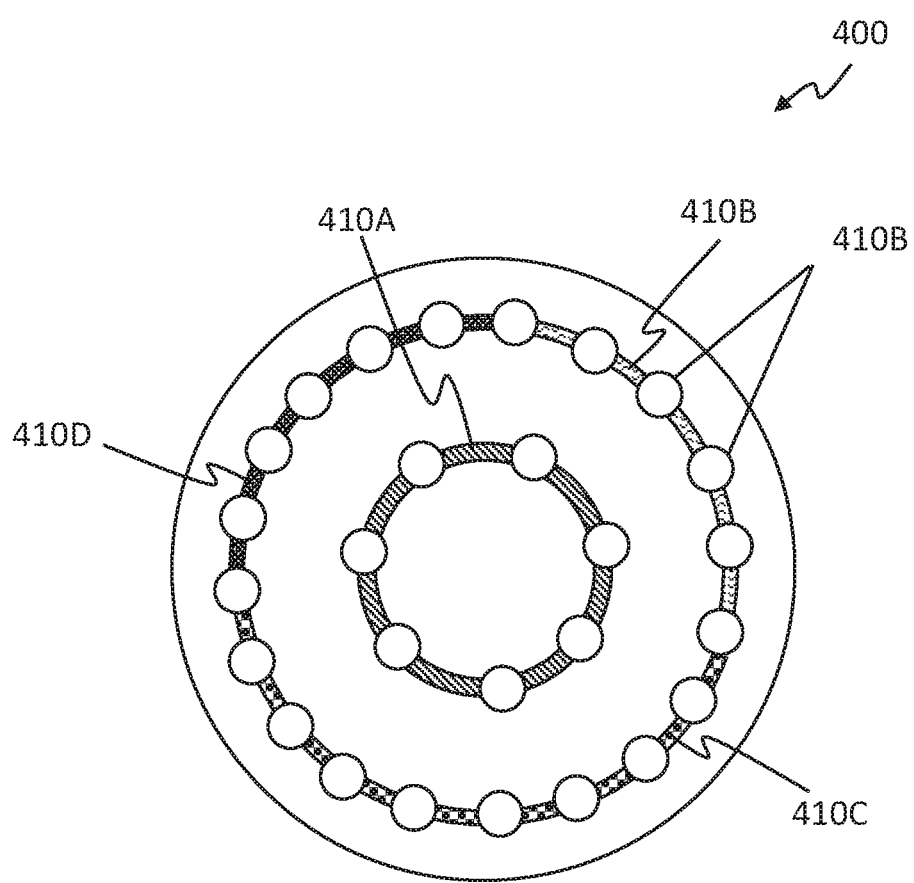
FIG. 4 depicts an exemplary variation of a package for containing daily supplements.

Alternatively, one or both of the housing portions 310A and 310B may include a recess configured to receive at least one packet (e.g., blister pack) or other arrangement of daily supplements. For example, the housing 110 may have a clamshell configuration having an internal volume for receiving one or more packets of daily supplements. FIG. 4 illustrates an exemplary blister pack 400 that may be inserted into a housing similar to that shown in FIGS. 3A and 3B.

The housing may be formed from any suitable material, such as paper (e.g., cardstock for suitable structural integrity), plastic, wood, metal, etc. The housing may be made as one integral piece (e.g., material cut into a suitable pattern and folded to form pockets, injection molded, milled, etc.) or multiple pieces that are assembled to form the housing.

Figure 5A:
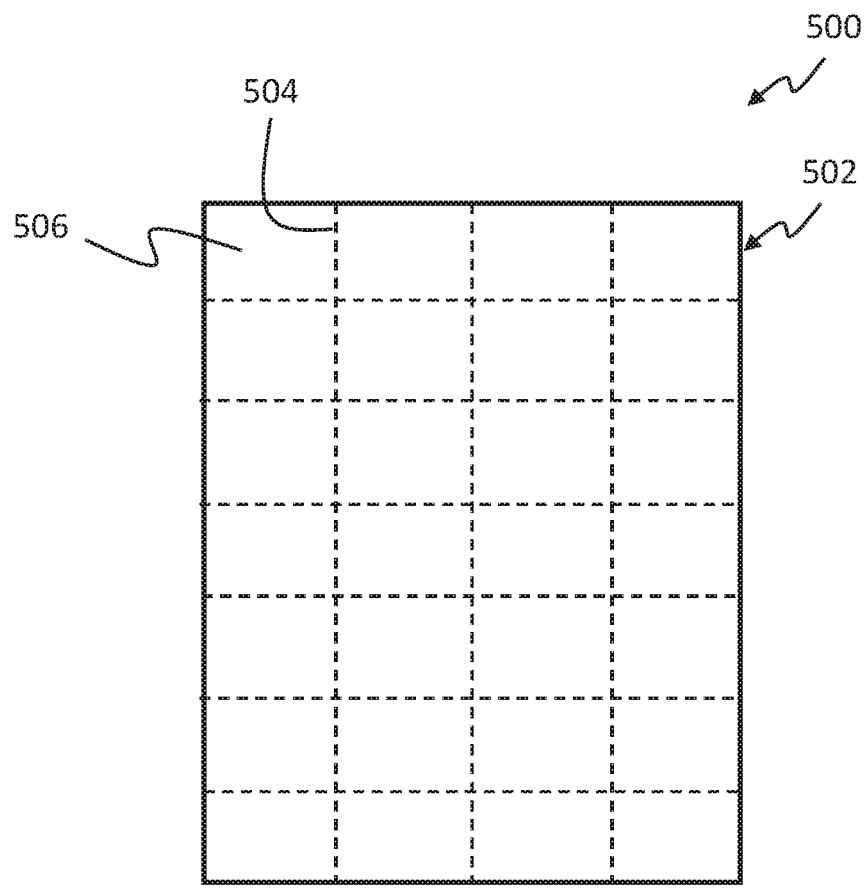
FIGS. 5A and 5B are plan and cross-sectional views, respectively, of another exemplary variation of a package for containing daily supplements.
Figure 5B:
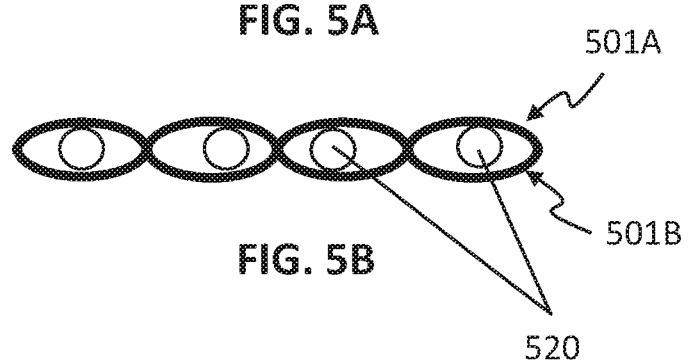

FIGS. 5A and 5B illustrate a plan view and a cross-sectional view, respectively, of an exemplary variation of kit 500 including a housing 502 for storing daily supplements. The housing 502 includes a plurality of quilted pockets 506. The quilted pockets 506 may be formed from one or more seams 504 that couple a first material surface 501A and a second material surface 501B in a quilted pattern. For example, the housing 502 may be made of fabric, and the quilted pockets 506 may be formed by sewing seams 504 in a grid or other pattern. As another example, the housing 502 may be made of plastic, and the quilted pockets 506 may be formed by heat-treating (e.g., welding) seams 504 in a grid or other suitable pattern. Each pocket 506 may contain at least one daily supplement 520, and the daily supplement 520 contained therein may be accessed by cutting, puncturing, popping, or otherwise opening the pocket 506. In some variations, the housing 502 may be transformed into a storage configuration, such as by rolling or folding the housing 502. The housing 502 may include a locking mechanism, such as a tie, fasteners (e.g., snaps, hook and loop fastener), wrap, etc. to secure the housing 502 in the storage configuration.

Arrangement of Daily Supplements

As described above, the kit includes daily supplements packaged in a single kit. In some variations, at least a portion of the daily supplements may be arranged in a packet insertable in a housing. For example, as shown in FIGS. 1B and 1C, at least a portion of the daily supplements may be arranged in one or more blister packs 120 insertable in a housing. A blister pack may compartmentalize the daily supplements such that the daily supplements are removed one (or any suitable number) at a time. A blister pack may have any suitable shape, such as a rectangle (e.g., the blister packs 120 shown in FIG. 1C) or circular (e.g., the blister pack 400 shown in FIG. 4), or square, elliptical, or other suitable polygonal shape. Within a blister pack, the daily supplements may be arranged in one or more rows, one or more rings, a spiral, or any suitable pattern.

Additionally or alternatively, some variations, at least a portion of the daily supplements may be arranged directly in the housing. For example, as described above with reference to FIG. 3B, at least some of the daily supplements may be arranged in wells. At least some of the wells may be covered with a seal (e.g., plastic film, foil, etc.) that may be peeled off or punctured to reveal and enable removal of the daily supplements each day. As another example, as described above with reference to FIGS. 5A and 5B, at least a portion of the daily supplements may be arranged in quilted compartments of a housing.

The daily supplements may be arranged (e.g., in a packet and/or in the housing) according to menstrual cycle. For example, the daily supplements may be grouped based on the time period in which they are designed to be ingested (e.g., daily supplements of a first type in a first group, daily supplements of a second type in a second group, etc.). Additionally or alternatively, the daily supplements may be sequentially arranged according to day of the menstrual cycle.

In some variations, the kit may include one or more labels identifying at least a portion of the daily supplements of various types according to menstrual cycle phase (e.g., time periods designated for different types of daily supplements). The first time period may correspond to menstruation phase of the menstrual cycle. The first time period may, for example, begin on about day 1 of the menstrual cycle (beginning with first day of menstruation) and extend through menstruation phase. In some variations, the first time period may be from day 1 to day 10, from day 1 to day 9, from day 1 to day 8, from day 1 to day 7, from day 1 to day 6, from day 1 to day 5, from day 1 to day 4, or from day 1 to day 3 of the menstrual cycle.

In some variations, the second time period may correspond to the proliferation or follicular phase of the menstrual cycle. The second time period may, for example, be from day 4 to day 13, from day 4 to day 12, from day 4 to day 11, from day 4 to day 10, from day 5 to day 13, from day 5 to day 12, from day 5 to day 11, from day 5 to day 10, from day 6 to day 13, from day 6 to day 12, from day 6 to day 11, from day 6 to day 10, from day 7 to day 13, from day 7 to day 12, from day 7 to day 11, from day 7 to day 10, from day 8 to day 13, from day 8 to day 12, from day 8 to day 11, or from day 8 to day 10 of the menstrual cycle.

In some variations, the third time period may correspond to ovulation and/or early luteal phase of the menstrual cycle. The third time period may, for example, be from day 11 to day 21, from day 11 to day 20, from day 12 to day 21, from day 12 to day 20, from day 13 to day 21, from day 13 to day 20, from day 14 to day 21, or from day 14 to day 20.

In some variations, the fourth time period may correspond to luteal phase and/or premenstrual portions of the menstrual cycle. The fourth time period may, for example, be from day 21 or day 22 to end of a menstrual cycle, such as from day 21 or day 22 to day 35, from day 21 or day 22 to day 34, from day 21 or day 22 to day 33, from day 21 or day 22 to day 32, from day 21 or day 22 to day 31, from day 21 or day 22 to day 30, from day 21 or day 22 to day 29, or from day 21 or day 22 to day 28.

In an example variation, the kit may include one or more labels identifying daily supplements throughout a 30-day period of time, including label(s) identifying a first portion of daily supplements (e.g., daily supplements of a first type as described above) for day 1 to day 5 of a cycle, label(s) identifying a second portion of daily supplements (e.g., daily supplements of a second type as described above) for day 6 to day 10 of a cycle, label(s) identifying a third portion of daily supplements (e.g., daily supplements of a third type as described above) for day 11 to day 20 of a cycle, and/or label(s) identifying a fourth portion of daily supplements (e.g., daily supplements of day 21 to day 30 of a cycle.

However, it should be understood that while the above-described time periods may be suitable for a general population of users, in some variations specific time periods for the different supplement types may be determined in a customized manner for a particular user. For example, a user's menstrual cycle duration and/or timing of different phases thereof may be determined based on user information such as calendaring of user symptoms and/or menstruation. Such user information may, for example, be gathered through a questionnaire or a suitable menstrual cycle tracking system (e.g., mobile application executed on a computing device). Accordingly, in some variations, a user-customized kit may include daily supplements arranged (e.g., number of daily supplements of each type) in any suitable manner based on the user's needs. For example, a user having a 28-day cycle may be supplied with a kit having daily supplements for 28 days (e.g., 28 capsules where each capsule is taken daily, or 56 capsules where two capsules are taken daily, etc.). As another example, a different user having a 30-day cycle may be supplied with a kit having daily supplements for 30 days (e.g., 30 capsules where each capsule is taken daily, or 60 capsules where two capsules are taken daily, etc.). As another example, a different user having a 35-day cycle may be supplied with a kit having daily supplements for 35 days (e.g., 35 capsules where each capsule is taken daily, or 70 capsules where two capsules are taken daily, etc.).

Figure 2A:
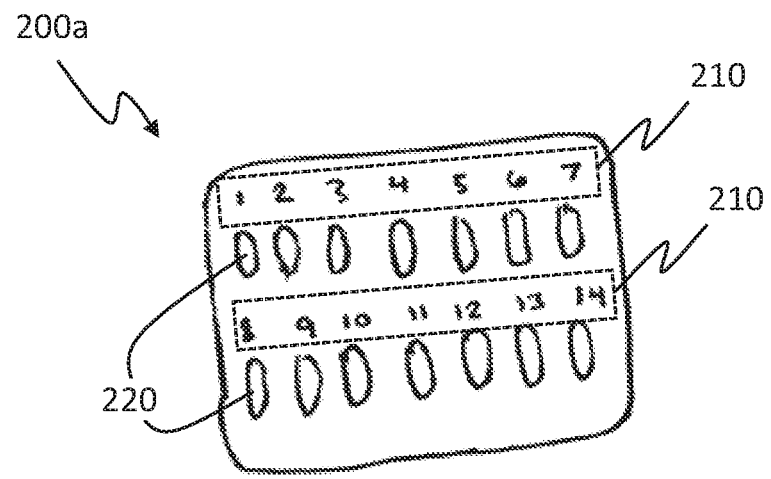
FIGS. 2A-2D depict exemplary variations of packages for containing daily supplements.

In some variations, the one or more labels may include one or more labels that instruct the ingesting of each daily supplement on a particular assigned day of the menstrual cycle. For example, FIG. 2A illustrates an exemplary blister pack 200a with labels 210 arranged adjacent to daily supplements 220. The labels 210 include numbers, where each number indicates a particular day of the menstrual cycle on which an associated daily supplement is designed to be ingested. Although FIG. 2A illustrates a blister pack with 14 supplements, it should be understood that a single blister pack may include any suitable number of supplements (e.g., 5, 7, 10, 14, 15, 28, 30, 35, etc.) labeled similarly. Furthermore, numerical labels may be specific calendar dates.

Figure 2B:
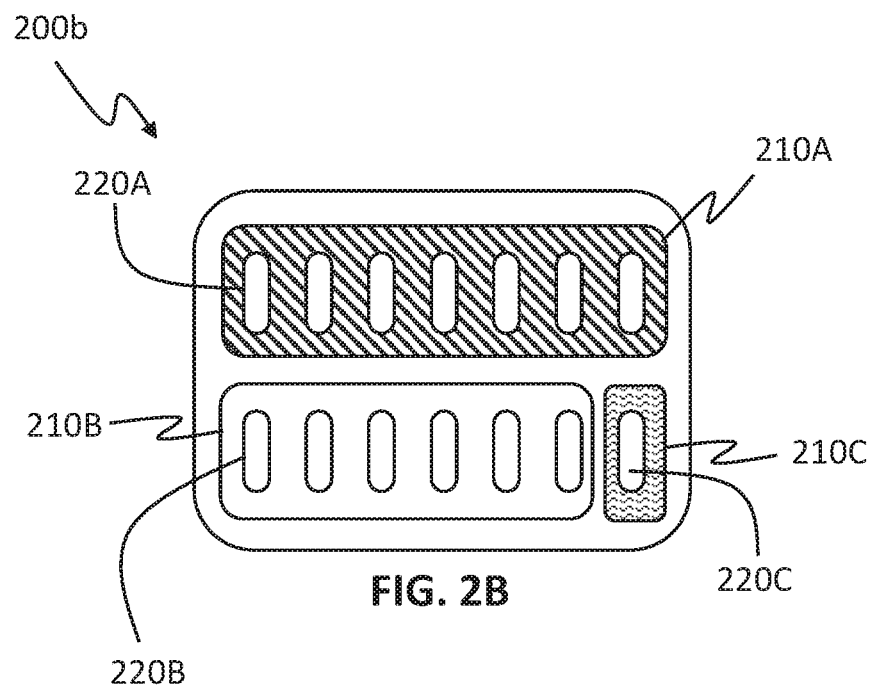

Additionally or alternatively, one or more labels in the kit may instruct the ingesting of each daily supplement during a time period or phase of the menstrual cycle. For example, FIG. 2B illustrates an exemplary blister pack 200b with labels 210A-210C arranged adjacent to daily supplements 220A-220B. The labels 210A-210C may have distinct appearances to identify which daily supplements are designed for ingestion in particular time periods. For example, the labels 210A-210C may be visually coded, such as with color (color-coded labels) or patterns. Additionally or alternatively, the labels 210A-210C may have any other suitable distinct features, such as textures. The labels 210A-210C indicate groups of daily supplements of different types. For example, label 210A surrounds a first group of daily supplements 220A which may be daily supplements of a first type (e.g., as described above) designed for ingestion during a first phase of a menstrual cycle. Similarly, label 210B surrounds a second group of daily supplements 220B which may be daily supplements of a second type, and label 210C surrounds a third group of daily supplements 220C which may be daily supplements of a fourth type. Although the blister pack 200b illustrates labels indicating daily supplements for three different time periods of a menstrual cycle, it should be understood that any suitable number of different time periods may be identified (e.g., 1, 2, 3, 4, etc.).

In some variations such as those described above with respect to FIGS. 2A and 2B, the one or more labels may be on the packet (e.g., blister pack) containing the daily supplements. The labels may be affixed to the packet (e.g., as stickers), printed, embossed, etched, or otherwise formed or attached to the packet in any suitable manner. Furthermore, it should be understood that any of the above label types may additionally or alternatively be on the housing (e.g., in variations in which the daily supplements are arranged directly in the housing). Even further, in some variations kit may include a processor and a display configured to display the one or more labels. The kit may be in communication with a clock (e.g., local clock or remote clock in wireless communication with the kit), such that the display may update to indicate calendar dates or other reminders (e.g., display "TODAY" or other reminder marker near the current day's supplement) to a user to ingest the daily supplement(s) per recommendations or instructions.

Figure 2C:
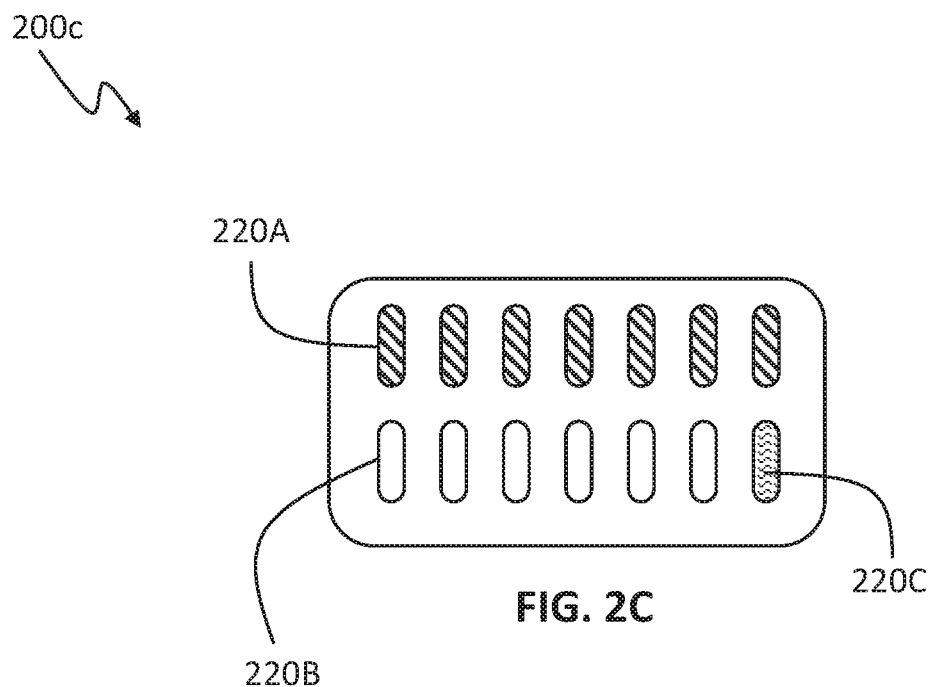
Figure 2D:
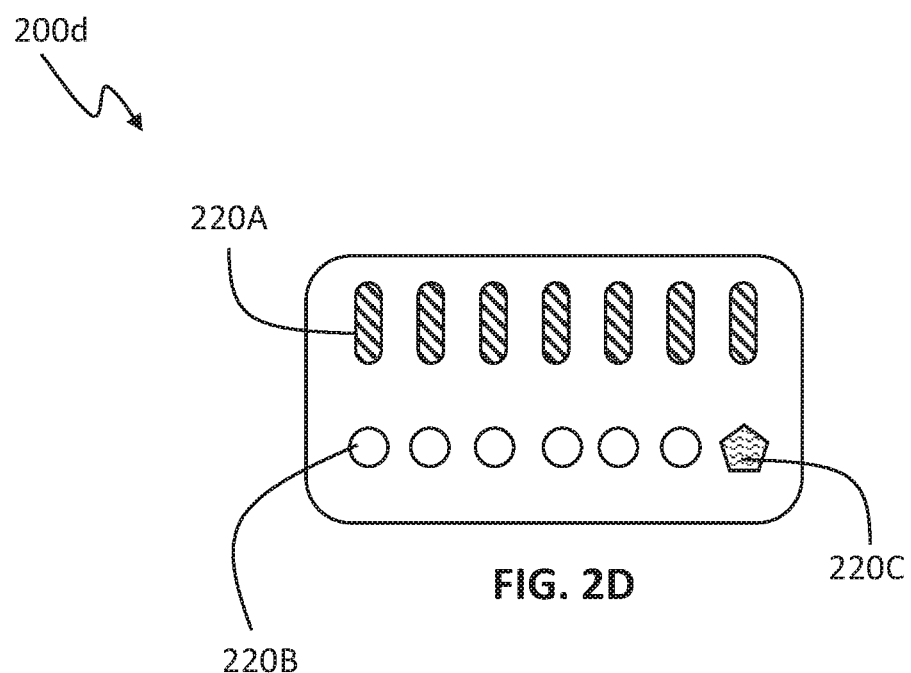

Additionally or alternatively, the one or more labels identifying at least a portion of the daily supplements may be embodied on the daily supplements themselves. In some variations, as shown in FIG. 2C, daily supplements may be visually coded based on type and intended time period for ingestion. For example, daily supplements of a first type 220A (designed for ingestion during a first time period of a menstrual cycle) may have a first color, daily supplements of a second type 220B (designed for ingestion during a second time period of a menstrual cycle) may have a second color, daily supplements of a third type 220C (designed for ingestion during a third time period of a menstrual cycle), and so on. Additionally or alternatively, daily supplements of different types may have different shapes (FIG. 2C) and/or textures. Similarly, the one or more labels identifying at least a portion of the daily supplements may be embodied in the shape of the wells of the blister pack (or housing).

Accordingly, the kit may easily communicate or instruct the various types of daily supplements for ingestion on designated days (or during designated portions) of a menstrual cycle, for example through a specific arrangement of daily supplements and/or labeling thereof. It should be understood that additional modes of instruction (e.g., on a shipping box containing the housing, an instructional insert contained in such a shipping box, other marketing materials such as on a website, communicated over email or in a mobile application executed on a mobile device, etc.) may additionally or alternatively be used to communicate when each of the various daily supplements should be ingested.

Thus, the kit helps enable a user to ingest the daily supplements in a suitable order (to ingest each type of supplement on a suitable day of their menstrual cycle), thereby enabling the supplements to work synergistically for supporting the user's health throughout a menstrual cycle.

Other Identifiers

In some variations, the kit may include one or more identifiers communicating additional information. For example, the kit may include one or more labels identifying a kit with an associated user. Such a user label may include, for example, a user name, a machine-readable code (e.g., bar code), a serial number, etc. A user label may be desirable, for example, to distinguish between different kits for different users in the same household and to help avoid confusion among users. Furthermore, as described above, in some variations a kit may be customized for a user based on user information (e.g., length of menstrual cycle, length of various phases of menstrual cycle), and a user label may help identify the kit for the appropriate user. Similar to the labels described above, a user label may be on the packet, housing, or other documentation associated therewith.

Methods

Methods for supporting health of a user throughout the user's menstrual cycle may include providing a kit as described above, where the kit includes daily supplements of various types to be ingested at respective time periods during the menstrual cycle. For example, the method may include providing one or more (e.g., at least two) daily supplements of a first type, providing one or more (e.g., at least two) daily supplements of a second type, instructing the user to ingest the daily supplements of the first type during the first time period of the menstrual cycle, and instructing the user to ingest the daily supplements of the second type during the second time period of the menstrual cycle. Furthermore, the method may include providing one or more (e.g., at least two) daily supplements of a third type, providing one or more (e.g., at least two) daily supplements of a third type, instructing the user to ingest the daily supplements of the third time period of the menstrual cycle, and instructing the user to ingest the daily supplements of the fourth type during the fourth time period of the menstrual cycle. The instructions for ingesting the various types of daily supplements may include instructing the user to ingest each type of daily supplement during at least two days of each respective time period of the menstrual cycle.

For example, similar to that described above, the daily supplements of the first type may be instructed for ingestion during at least a portion of the period from day 1 to about day 7 of the menstrual cycle (e.g., from day 1 to day 3 or day 5 or day 7), where day 1 is the beginning of menstruation. Additionally or alternatively, the daily supplements of the second type may be instructed for ingestion during at least a portion of the period from about day 4 to about day 13 of the menstrual cycle (e.g., from day 4 or day 6 or day 8 to day 10 or day 11 or day 12 or day 13). Additionally or alternatively, the daily supplements of the third type may be instructed for ingestion during at least a portion of the period from about day 11 to about day 21 (e.g., from day 11 or day 12 or day 13 or day 14 to day 21). Additionally or alternatively, the daily supplements of the fourth type may be instructed for ingestion during at least a portion of the period from about day 22 to about day 35 or other end of the menstrual cycle (e.g., from day 22 to day 28 or day 30 or day 32 or day 35).

The instructions for ingesting the various types of daily supplements may be provided in any suitable manner. For example, the instructions may be in the form of one or more labels on or in a kit including the daily supplements (e.g., as described above with respect to FIGS. 1A-5B). Additionally or alternatively, the instructions may be in the form of packaging materials such as printed on a box including the kit, printed on informational inserts provided with such a box, or provided electronically such as displayed on a website, in an email or electronic notification, in a mobile application executed on a mobile device, etc.

EXAMPLES

The following examples are merely illustrative and are not meant to limit any aspects of the present disclosure in any way.

Example 1: Table 1A illustrates an exemplary formulation for a daily supplement of a first type (Phase One daily supplement) including chelated iron or ferrous sulfate, ascorbic acid, and cramp bark.

TABLE 1A

Exemplary formulation for Phase One daily supplement

| Nutrient | Amount Per Unit Dose |
|---|---|
| Chelated iron or ferrous sulfate | 10 mg |
| Ascorbic acid | 67 mg |
| Cramp bark | 300 mg |

Example 2: Table 1B illustrates another exemplary formulation for a daily supplement of a first type (a Phase One daily supplement). This exemplary formulation is similar to that shown in Table 1A except that it further includes ginger root.

TABLE 1B

Exemplary formulation for Phase One daily supplement

| Nutrient | Amount Per Unit Dose |
|---|---|
| Chelated iron or ferrous sulfate | 10 mg |
| Ascorbic acid | 67 mg |
| Cramp bark | 300 mg |
| Ginger root | 150 mg |

Example 3: Table 1C illustrates another exemplary formulation for a daily supplement of a first type (a Phase One daily supplement) including ascorbic acid, chelated iron, cramp bark, and various additives.

TABLE 1C

Exemplary formulation for Phase One daily supplement

| Nutrient/Additive | Amount Per Unit Dose |
|---|---|
| Ascorbic acid | 67 mg |
| Iron bisglycinate chelate 20% Fe | 10 mg |
| Cramp bark | 150 mg |
| Silica (Cabosil ® M5) | 14 mg |
| Magnesium stearate | 12 mg |
| Microcrystalline cellulose | 50 mg |
| Silica (Zeofree ® 80) | 10 mg |

Example 4: Table 2A illustrates an exemplary formulation for a daily supplement of a second type (a Phase Two daily supplement) including methylcobalamin, methyl folate or folate, iodine, Vitamin $D_3$ or $D_2$, and Vitamin $K_2$ or $K_3$.

TABLE 2A

Exemplary formulation for Phase Two daily supplement

| Nutrient | Amount Per Unit Dose |
|---|---|
| Vitamin $B_{12}$ (methylcobalamin) | 1000 mcg |
| Methyl folate or folate | 400 mcg |
| Iodine | 150 mcg |
| Vitamin $D_3$ or $D_2$ | 1000 IU |
| Vitamin $K_2$ or $K_3$ | 100 IU |

Example 5: Table 2B illustrates an exemplary formulation for a daily supplement of a second type (a Phase Two daily supplement). This exemplary formulation is similar to that shown in Table 2A except that it further includes selenium.

TABLE 2B

Exemplary formulation for Phase Two daily supplement

| Nutrient | Amount Per Unit Dose |
|---|---|
| Vitamin $B_{12}$ (methylcobalamin) | 1000 mcg |
| Methyl folate or folate | 400 mcg |
| Iodine | 150 mcg |
| Vitamin $D_3$ or $D_2$ | 1000 IU |
| Vitamin $K_2$ or $K_3$ | 100 IU |
| Selenium | 100 mcg |

Example 6: Table 2C illustrates an exemplary formulation for a daily supplement of a second type (a Phase Two daily supplement) including methylcobalamin, methyl folate, selenium, Vitamin $D_3$, Vitamin $K_2$, and iodine.

TABLE 2C

Exemplary formulation for Phase Two daily supplement

| Nutrient/Additive | Amount Per Unit Dose |
|---|---|
| Vitamin $B_{12}$ (methylcobalamin 100%) | 1 mg |
| Methyl folate (calcium 5-methyltetrahydrofolate (5-MTHF-Ca)) | 0.4 mg |
| Selenium AAC (0.2% Se) | 0.1 mg |
| Vitamin $D_3$ (100,000 IU/g, cholecalciferol) | 1000 IU |
| Vitamin $K_2$ 0.1% (menaquinone-7) | 0.1 mg |
| Kelp powder (0.3% I) | 0.15 mg |

Example 7: Table 3A illustrates an exemplary formulation for a daily supplement of a third type (a Phase Three daily supplement) including chaste berry and milk thistle.

TABLE 3A

Exemplary formulation for Phase Three daily supplement

| Nutrient | Amount Per Unit Dose |
|---|---|
| Chaste berry | 60 mg |
| Milk thistle | 140 mg |

Example 8: Table 3B illustrates an exemplary formulation for a daily supplement of a third type (a Phase Three daily supplement) including chaste berry, milk thistle, and various additives.

TABLE 3B

Exemplary formulation for Phase Three daily supplement

| Nutrient/Additive | Amount Per Unit Dose |
|---|---|
| Chaste berry (4:1 extract ratio) | 100 mg |
| Milk thistle (extract, 80% silymarin) | 100 mg |
| Magnesium stearate | 5 mg |
| Microcrystalline cellulose | 210 mg |
| Silica (Zeofree ® 80) | 5 mg |

Example 9: Table 4A illustrates an exemplary formulation for a daily supplement of a fourth type (a Phase Four daily supplement) including Vitamin $B_6$, white willow bark, Vitamin E, and *Gingko biloba*.

TABLE 4A

Exemplary formulation for Phase Four daily supplement

| Nutrient | Amount Per Unit Dose |
|---|---|
| Vitamin $B_6$ | 50 mg |
| White willow bark | 240 mg |
| Vitamin E | 400 IU |
| Gingko biloba | 120 mg |

Example 10: Table 4B illustrates an exemplary formulation for a daily supplement of a fourth type (a Phase Four daily supplement) including Vitamin $B_6$, white willow bark, DHA, ginger root, capsaicin, chamomile, and valerian root.

TABLE 4B

Exemplary formulation for Phase Four daily supplement

| Nutrient | Amount Per Unit Dose |
|---|---|
| Vitamin $B_6$ | 50 mg |
| White willow bark | 240 mg |
| DHA | 250 mg |
| Ginger root | 150 mg |
| Capsaicin | 150 mg |
| Chamomile | 220 mg |
| Valerian root | 300 mg |

Example 11: Table 4C illustrates an exemplary formulation for a daily supplement of a fourth type (a Phase Four daily supplement) including Vitamin $B_6$, white willow bark, and magnesium citrate or magnesium glycinate.

TABLE 4C

Exemplary formulation for Phase Four daily supplement

| Nutrient | Amount Per Unit Dose |
|---|---|
| Vitamin $B_6$ | 50 mg |
| White willow bark | 240 mg |
| Magnesium citrate or magnesium glycinate | 200 mg |

Example 12: Table 4D illustrates an exemplary formulation for a daily supplement of a fourth type (a Phase Four daily supplement) including Vitamin $B_6$, Vitamin E, *Gingko biloba*, white willow bark, and various additives.

TABLE 4D

Exemplary formulation for Phase Four daily supplement

| Nutrient/Additive | Amount Per Unit Dose |
|---|---|
| Vitamin $B_6$ (pyridoxal 5-phosphate (67% pyridoxine) | 50 mg |
| Vitamin E (d-alpha tocopheryl succinate, 1185 IU/mg d-alpha tocopherol) | 150 IU |
| Gingko biloba (extract, 24% flavonoids) | 120 mg |
| White willow bark (extract, 25% salicin) | 120 mg |
| Magnesium stearate | 20 mg |
| Microcrystalline cellulose | 50 mg |
| Silica (Sipernat® 22 S) | 3 mg |

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A kit for supporting health of a user throughout the user's menstrual cycle, comprising:
at least two daily supplements of a first type configured to support health of the user throughout a menstruation phase of the user's menstrual cycle;
at least two daily supplements of a second type, the second type different from the first type and configured to support health of the user throughout a follicular phase of the user's menstrual cycle;
at least two daily supplements of a third type, the third type different from the first and second types and configured to support health of the user throughout an ovulation phase and throughout a first portion of a luteal phase of the user's menstrual cycle; and
at least two daily supplements of a fourth type, the fourth type different from the first, second, and third types and configured to support health of the user throughout a second portion of the luteal phase and throughout a premenstrual phase of the user's menstrual cycle,
wherein the daily supplements of the first type, second type, third type, and fourth type each has a respective single nutrient composition in a unit dose and are packaged together in a single kit according to menstrual cycle phase.

2. The kit of claim 1, wherein the daily supplements of the first type comprise one or more nutrients selected from the group consisting of iron, Vitamin C, cramp bark, and ginger root.

3. The kit of claim 1, wherein the daily supplements of the second type comprise one or more nutrients selected from the group consisting of Vitamin $B_{12}$, folate, iodine, Vitamin $D_2$, Vitamin $D_3$, Vitamin $K_2$, Vitamin $K_3$, and selenium.

4. The kit of claim 1, wherein the daily supplements of the third type comprise one or more nutrients selected from the group consisting of chaste berry and milk thistle.

5. The kit of claim 1, wherein the daily supplements of the fourth type comprise one or more nutrients selected from the group consisting of Vitamin $B_6$, Vitamin E, *Gingko biloba*, white willow bark, an omega-3 fatty acid, ginger root, capsaicin, chamomile, valerian root, and magnesium.

6. The kit of claim 1, wherein:
the daily supplements of the first type comprise a first unit dose comprising: from about 5 mg to about 15 mg chelated iron or ferrous sulfate, from about 50 to 500 mg Vitamin C, and from about 100 to 500 mg of cramp bark,
the daily supplements of the second type comprise a second unit dose comprising: from about 10 mcg to about 2500 mcg of Vitamin $B_{12}$, from about 10 mcg to about 800 mcg of methyl folate or folate, from about 100 IU to about 2500 IU of Vitamin $D_2$ or Vitamin $D_3$, and from about 10 mcg to about 200 mcg of Vitamin $K_2$ or $K_3$,
the daily supplements of the third type comprise a third unit dose comprising: from about 40 mg to about 150 mg of chaste berry, and from about 50 mg to about 400 mg of milk thistle, and
the daily supplements of the fourth type comprise a fourth unit dose comprising from about 5 mg to about 100 mg of Vitamin $B_6$, and from about 80 mg to about 500 mg of white willow bark.

7. The kit of claim 6, wherein the first unit dose further comprises from about 50 mg to about 300 mg ginger root and wherein the second unit dose further comprises from about 50 mcg to about 200 mcg of selenium.

8. The kit of claim 6, wherein the fourth unit dose further comprises from about 100 IU to about 500 IU of Vitamin E, and from about 80 mg to about 160 mg of *Gingko biloba*.

9. The kit of claim 6, wherein the fourth unit dose further comprises about 250 mg of DHA, about 150 mg of ginger root, about 150 mg of capsaicin, about 220 mg of chamomile, and about 300 mg of valerian root.

10. The kit of claim 1, wherein the daily supplements of the first type and the daily supplements of the second type are sequentially arranged in a blister pack according to menstrual cycle phase.

11. The kit of claim 10, further comprising a reclosable housing containing the blister pack.

12. The kit of claim 1, further comprising one or more labels identifying at least a portion of the daily supplements of the first type and the daily supplements of the second type according to menstrual cycle phase.

13. The kit of claim 12, wherein the one or more labels comprises a plurality of labels identifying each daily supplement of the first type and each daily supplement of the second type for ingesting on a respective assigned day of the menstrual cycle.

14. The kit of claim 12, wherein the one or more labels comprise at least one of:
one or more labels identifying the daily supplements of the first type for ingesting during at least a portion of the time period from day 1 to day 7 of the menstrual cycle;
one or more labels identifying the daily supplements of the second type for ingesting during at least a portion of the time period from day 4 to day 13 of the menstrual cycle,
one or more labels identifying daily supplements of the third type for ingesting during at least a portion of the time period from day 11 to day 21 of the menstrual cycle, and
one or more labels identifying daily supplements of the fourth type for ingesting during at least a portion of the time period from day 22 to day 35 of the menstrual cycle.

15. The kit of claim 14, wherein the one or more labels comprise:
one or more labels identifying the daily supplements of the first type for ingesting one daily supplement of the first type each throughout day 1 to day 5 of the menstrual cycle;
one or more labels identifying the daily supplements of the second type for ingesting throughout day 6 to day 10 of the menstrual cycle;
one or more labels identifying the daily supplements of the third type for ingesting throughout day 11 to day 20 of the menstrual cycle; and
one or more labels identifying the daily supplements of the fourth type for ingesting throughout day 21 to day 30 of the menstrual cycle.

16. The kit of claim 1, wherein the daily supplements of the first type, second type, third type, and fourth type each has a respective single nutrient composition contained in a single capsule.

17. A method for supporting health of a user throughout the user's menstrual cycle, comprising:
providing at least two daily supplements of a first type;
providing at least two daily supplements of a second type;
providing at least two daily supplements of a third type;
providing at least two daily supplements of a fourth type; and
instructing the user to ingest the daily supplements of the first type during at least two days of a first time period corresponding to a menstruation phase of the menstrual cycle, to ingest the daily supplements of the second type during at least two days of a second time period corresponding to a follicular phase of the menstrual cycle, to ingest the daily supplements of the third type during at least two days of a third time period corresponding to an ovulation phase and a first portion of a luteal phase of the menstrual cycle, and to ingest the daily supplements of the fourth type during at least two days of a fourth time period corresponding to a second portion of the luteal phase and a premenstrual phase of the menstrual cycle,
wherein the daily supplements of the first type, second type, third type, and fourth type each has a respective single nutrient composition in a single unit dose.

18. The method of claim 17, wherein:
the first time period comprises at least a portion of the period from day 1 to day 7 of the menstrual cycle,
the second time period comprises at least a portion of the period from day 4 to day 13 of the menstrual cycle,
the third time period comprises at least a portion of the period from day 11 to day 21 of the menstrual cycle, and
the fourth time period comprises at least a portion of the period from day 22 to day 35 of the menstrual cycle.

19. The method of claim 17, wherein:
the daily supplements of the first type comprise one or more nutrients selected from the group consisting of iron, Vitamin C, cramp bark, and ginger root,
the daily supplements of the second type comprise one or more nutrients selected from the group consisting of Vitamin $B_{12}$, folate, iodine, Vitamin $D_2$, Vitamin $D_3$, Vitamin $K_2$, Vitamin $K_3$, and selenium,
the daily supplements of the third type comprise one or more nutrients selected from the group consisting of chaste berry and milk thistle, and
the daily supplements of the fourth type comprise one or more nutrients selected from the group consisting of Vitamin $B_6$, Vitamin E, *Gingko biloba*, white willow bark, an omega-3 fatty acid, ginger root, capsaicin, chamomile, valerian root, and magnesium.

20. The method of claim 18, wherein:
the first time period is throughout day 1 to day 5 of the menstrual cycle;
the second time period is throughout day 6 to day 10 of the menstrual cycle;
the third time period is throughout day 11 to day 20 of the menstrual cycle; and
the fourth time period is throughout day 21 to day 30 of the menstrual cycle.

* * * * *